(12) United States Patent
Brackett

(10) Patent No.: US 7,116,807 B1
(45) Date of Patent: Oct. 3, 2006

(54) METHOD AND APPARATUS FOR LINKING IMAGES AND REPORTS AT REMOTE VIEW STATION

(75) Inventor: Charles Cameron Brackett, Brookfield, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 667 days.

(21) Appl. No.: 09/667,889

(22) Filed: Sep. 22, 2000

(51) Int. Cl.
*G06K 9/00* (2006.01)

(52) U.S. Cl. .......................... 382/128; 378/4; 378/901

(58) Field of Classification Search ................ 382/128, 382/129, 130, 131, 132, 133, 134; 378/8, 378/87, 4, 21–27, 46, 90, 92, 94.08, 98.6, 378/98.9, 101, 140, 901; 345/505, 564; 709/219; 600/440, 441, 443, 447, 455, 458, 459, 508, 600/437, 425; 358/468, 474, 486, 487, 494, 358/505; 379/9.04; 250/363.04, 370.09
See application file for complete search history.

(56) References Cited

U.S. PATENT DOCUMENTS

| | | | | |
|---|---|---|---|---|
| 4,764,870 A | * | 8/1988 | Haskin | 348/443 |
| 5,603,323 A | * | 2/1997 | Pflugrath et al. | 600/437 |
| 5,646,416 A | * | 7/1997 | Van de Velde | 250/584 |
| 5,795,297 A | * | 8/1998 | Daigle | 600/447 |
| 5,938,607 A | * | 8/1999 | Jago et al. | 600/437 |
| 6,032,120 A | * | 2/2000 | Rock et al. | 705/2 |
| 6,303,924 B1 | * | 10/2001 | Adan et al. | 250/221 |
| 6,325,759 B1 | * | 12/2001 | Pelissier | 600/443 |

* cited by examiner

*Primary Examiner*—Kanjibhai Patel
*Assistant Examiner*—Abolfazl Tabatabai
(74) *Attorney, Agent, or Firm*—Ostrager Chong Flaherty & Broitman P.C.

(57) ABSTRACT

A scanner is programmed with the capability to send images via a parallel port and report data via a serial port to a remote device, both images and report data being identified by the same study identifier. In particular, the images are sent out an Ethernet port in DICOM format, while the report data is sent out an RS232 port in ASCII format. The scanner preferably includes memory storing a frame of image data belonging to a study and report data belonging to said study; a parallel port; a serial port; and a computer programmed to perform the following steps: joining a study identifier with the frame of image data; sending the frame of image data and the study identifier in a first format out the parallel port; joining the study identifier with the report data; and sending the report data and the study identifier in a second format out the serial port.

24 Claims, 6 Drawing Sheets

NEW PATIENT

Erase patient info and measurements? (Y=Yes N=No & Return) ☐

Exam Category (SET to select)

| * GENERAL IMAGING | | VASCULAR |
| OB/GYN | | PEDIATRIC |
| SMALL PARTS | | |

PATIENT NAME

LAST: _____ FIRST: _____ MIDDLE INITIAL: ☐ ☐

PT ID: _____ SEX (M OR F): [M]

Accession # _____

DOB (MM/DD/YYYY): [0/] [0/] [0/]

HISTORY: _____

REF MD: _____  OPERATOR ID: _____

TKBL/RET to position    SET to select    ROI Size to page    EXIT to quit

FIG.4

GE MEDICAL SYSTEMS                                  OB-1 SUMMARY
                                        LMP:   /   /      AGE:    12/05/99
REF MD:                                 G O P O A O E O*
HISTORY:
      GA(LMP):                          EDD(LMP):   /   /
Ultrasound Age:           +/−           Ultrasound EDD:   /   /

ANATOMICAL SURVEY          Fetal HR         bpm
ANATOMY               IMAGED  APPEARANCE
Gestational Sac        Y/N  |   |   |   |   |   |   |   |   |
Yolk Sac               Y/N  |   |   |   |   |   |   |   |   |
Heart Motion           Y/N  |   |   |   |   |   |   |   |   |
Right Adnexa           Y/N  |   |   |   |   |   |   |   |   |
Left Adnexa            Y/N  |   |   |   |   |   |   |   |   |
‡‡‡‡                   Y/N
****                   Y/N
‡‡‡‡                   Y/N
****                   Y/N
                                COMMENTS TKBL/RET to position    WORD DEL to delete          EXIT to save

FIG.5

METHOD AND APPARATUS FOR LINKING IMAGES AND REPORTS AT REMOTE VIEW STATION

FIELD OF THE INVENTION

This invention generally relates to imaging systems which communicate with remote devices via networks. In particular, the invention relates to the transfer of digital images and reports from an imaging system to remote devices for archiving, viewing and/or printing.

BACKGROUND OF THE INVENTION

In addition to storing images internally, modern imaging systems need to be able to transfer images to various types of remote devices via a communications network. To successfully transfer images, the relevant networking features of the imager must be compatible with the networking features of the destination remote device. In particular, the imager must place the data to be transferred in a format which can be handled by the destination remote device. An attempt to accomplish the foregoing is the adoption of the DICOM (Digital Imaging and Communications in Medicine) standards, which specify the conformance requirements for the relevant networking features. The DICOM standards are intended for use in communicating medical digital images among printers, workstations, acquisition modules (such as an ultrasound imaging system) and file servers. The acquisition module is programmed to transfer data in a format which complies with the DICOM standards, while the receiving device is programmed to receive data which has been formatted in compliance with those same DICOM standards.

The DICOM system is designed to facilitate the communication of digital images of different types, e.g., X-ray, computerized tomography, magnetic resonance and ultrasound imaging. In an ultrasound imager having conventional DICOM capability, three local real-world activities occur: Image Send, Image Print and Remote Verification. Image Send and Image Print can be done in either automatic or manual mode. Verification of remote DICOM devices configured on the ultrasound imager is performed when the imager is powered up or when requested by the system operator.

All DICOM activities are handled in a queued manner by application software running on a host computer incorporated in the imager. In one type of ultrasound imager, the user can select any image in cine memory to be sent in DICOM format via a local area network (LAN) to a remote device having DICOM capability. The host computer of the ultrasound imaging system is programmed with DICOM system software which facilitates transmission of image frames from the cine memory to the remote DICOM device via the host computer hard disk and the LAN.

In the conventional ultrasound imager, Image Send can be used in automatic or manual mode, depending on the user configuration. When automatic mode is configured, console keys are used to capture the image and to store it on the hard disk. The request is queued to a DICOM queue manager (preferably implemented in software), which requests an association with the destination remote device. After the association with the remote device has been opened, the queue manager "pushes" the image to the remote device without user intervention. The transfer is done in the background while scanning or other operator activities continue. In manual mode, the captured images are archived on the hard disk or on a MOD during the exam(s). Upon completion of the exam(s) the images are tagged using an archive menu and queued to any of the network devices that have been configured on the imager. The images are sent sequentially in the background while scanning or other operator activities proceed. Image Print works much the same way as Image Send, in both automatic and manual modes, the only difference being that the destination device is a printer.

In addition to the digitized image (i.e., pixel data), the DICOM object transferred from the ultrasound imager also includes an image header. The image header includes an identifier which uniquely identifies the study that the transferred image is part of. DICOM has defined a unique number for each and every study. Every DICOM image in a study must have this number attached to it. This unique identifier defines all images associated with the identified study. The image header also includes attribute information extracted from a pre-stored configuration file. For example, the attribute information may include patient attributes (e.g., patient name and patient identification number), exam attributes (e.g., exam description and exam date), series attributes (e.g., modality type and series date), and image attributes (e.g., image type and numbers of rows and columns).

The DICOM images constructed by an imaging system can be sent over a network to a viewing station or to a picture archiving and communications system (PACS) having a viewing station. The images are sent via an Ethernet port incorporated on the imaging system. It is also known to send reports from the imaging system to the viewing station via a serial port, also incorporated on the imaging system. Typically the serial port transmits and receives data in accordance with the RS232 protocol.

The off-line view station can be used to display the images and reports received from the imaging system. However, one problem is that, while DICOM defines the standard for transmitting images and data along with providing the necessary information to link all associated information with a study, it does not define any RS232 protocols for transmitting report data. Therefore, there is no standard that demonstrates the ability to link RS232 data with a DICOM study. Many companies have developed their own mechanism for transmitting report data via an RS232 interface. Also there are companies that have developed software to receive this RS232 data on a personal computer. The problem is that the companies that have developed the reporting software on the receiving personal computer cannot guarantee that the report data received is related to the DICOM images received. In other words, there is no way to accurately link the report data to a study (comprising a series of images) on a view station or PACS. Some companies have created a proprietary method of linking images and report data that is based on time and video capture, thereby losing much of the associated study information.

In one known ultrasound imaging system, whenever a study is begun, a unique Study Identifier is generated for that study. DICOM refers to this as the Study Instance UID. Each image that is taken during that study will have the Study Instance UID placed in the image header. Also found in that same image header are: Patient Name, Patient ID, Accession Number (a RIS-generated number which identifies the order for the study), Study Date, Study Time, and Patient's Date of Birth. During the exam, the sonographer may make measurements and comments about one or a group of images. The sonographer may also produce information or make comments about the entire exam. This information is placed on the report screen of the scanner. In the known ultrasound imaging system, the sonographer can take a screen shot of the report screen and send it as a DICOM image to the view station. Although that image has a header, that header does not contain the measurement data and other report data. That data only appears on the view station display screen as an image or screen shot. The receiving computer is unable to recognize the measurement data and other report data which are embedded in the image. Thus, the receiving computer is unable to automatically interpret and process the measurement data. For example, several companies sell software applications which receive the measurement data, input it automatically into a database, where it can be retrieved for use in generating reports, re-calculating the data, etc.

There is a need for a method and an apparatus that would allow report data to be sent out the serial port of an imaging system to a view station in such a way that the report data can be automatically linked to the images (sent out via a different port) with which the report data is associated.

SUMMARY OF THE INVENTION

The present invention is directed to an imager or scanner which is programmed with the capability to send images via a parallel port and report data via a serial port to a remote device, both images and report data being identified by the same study identifier. In particular, the images are sent out the parallel port in DICOM format, while the report data is sent out the serial port in ASCII format.

The invention is also directed to a receiving device having reporting software that uses the Study Instance UID transmitted with the RS232 data to ensure accuracy in linking the RS232 report data to the related DICOM images. In the case of old scanners in which the transmitted report data will not have a Study Instance UID in the report data, the view station software will search the view station database for any DICOM images that have attribute data which matches or nearly matches the attribute data attached to the received report data. In accordance with the preferred embodiment, the following items are compared: Patient Name, Patient ID, Accession Number, Study Date, Study Time and Patient's Date of Birth. For each DICOM image that has data which almost matches all of the above-listed data, a dialogue box will appear on the screen of the view station, prompting the user to manually match the report with the image. Once the user has done so, the Study Instance UID received in the DICOM protocol for those images will be added to the received report data (in ASCII format), thereby creating a permanent link between the report data and the images. This solution will provide an accurate link between studies (DICOM images and information) and report information without the need to update the existing software of any scanner which lacks the ability to transmit the Study Instance UID in ASCII format as part of report data transmitted via the serial port. For any scanner that is programmed to automatically attach the Study Instance UID to any ASCII report data, the view station can match images to reports by simply matching the Study Instance UIDs.

Although the preferred embodiment of the invention is disclosed below in the context of systems which send images in DICOM format via a parallel port and report data in RS232 format via a serial port to a destination device, it will be appreciated that the broad concept of the invention has application in any system whereby images are transmitted to a destination device via a parallel port in one format and report data is transmitted to the same device via a serial port in another format.

BRIEF DESCRIPTION OF THE DRAWINGS

FIG. 4 is a schematic reproducing a "New Patient" menu which can be called up on the display monitor of the imaging system in order to start a new patient exam.

FIG. 5 is a schematic reproducing a "Report" menu which appears on the display monitor of the imaging system in response to actuation of the Report button on the operator interface.

DETAILED DESCRIPTION OF THE PREFERRED EMBODIMENTS

Figure 1:
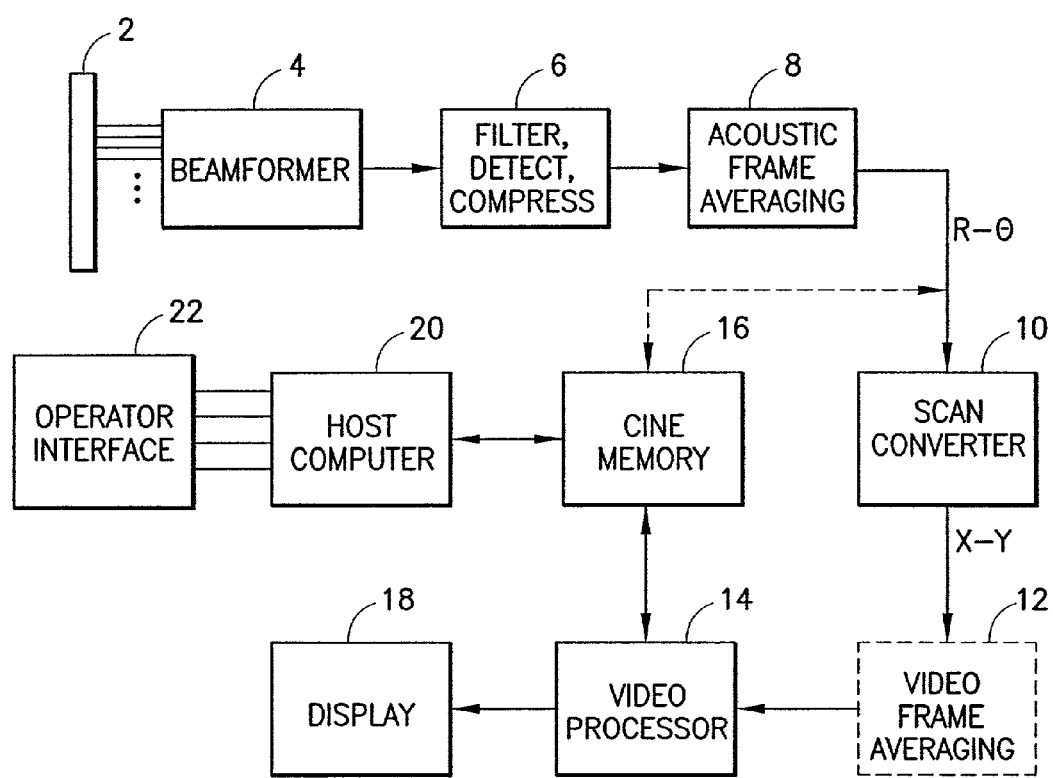
FIG. 1 is a block diagram generally depicting portions of a conventional ultrasound imaging system of the type which can be programmed to have DICOM capability.

FIG. 1 shows a conventional computerized ultrasound imaging system which can be programmed to communicate with remote devices over a network in conformance with the DICOM standards. The type of imaging system depicted in FIG. 1 creates two-dimensional B-mode images of tissue in which the brightness of a pixel is based on the intensity of the echo return. The basic signal processing chain is as follows.

An ultrasound transducer array 2 is activated to by a transmitter in a beamformer 4 to transmit an acoustic burst which is focused at a point along a scan line. The return RF signals are detected by the transducer elements and then dynamically focused to form a receive beam by a receiver in the beamformer 4. The receive beamformer output data (I/Q or RF) for each scan line is passed through a B-mode processing chain 6, which preferably includes demodulation, filtering, envelope detection, logarithmic compression and edge enhancement.

Depending on the scan geometry, up to a few hundred receive vectors may be used to form a single acoustic image frame. To smooth the temporal transition from one acoustic frame to the next, some acoustic frame averaging 8 may be performed before scan conversion. In general, the log-compressed display data is converted by the scan converter 10 into X-Y format for video display. On some systems, frame averaging may be performed on the X-Y data (indicated by dashed block 12) rather than the acoustic frames before scan conversion, and sometimes duplicate video frames may be inserted between acoustic frames in order to achieve a given video display frame rate. The scan-converted frames are passed to a video processor 14, which maps the video data using a gray-scale mapping. The gray-scaled image frames are then sent to a video monitor 18 for display.

System control is centered in a host computer 20, which accepts operator inputs through an operator interface 22 and in turn controls the various subsystems. (In FIG. 1, only the image data transfer paths are depicted.) The operator interface comprises a keyboard, a trackball, a multiplicity of pushbuttons, and other input devices such as sliding and rotary knobs.

During imaging, a long sequence of the most recent images are stored and continuously updated automatically in a cine memory 16. Some systems are designed to save the R-θ acoustic images (this data path is indicated by the dashed line in FIG. 1), while other systems store the X-Y video images. The image loop stored in cine memory 16 can be reviewed via trackball control, and a section of the image loop can be selected for hard disk storage.

Figure 2:
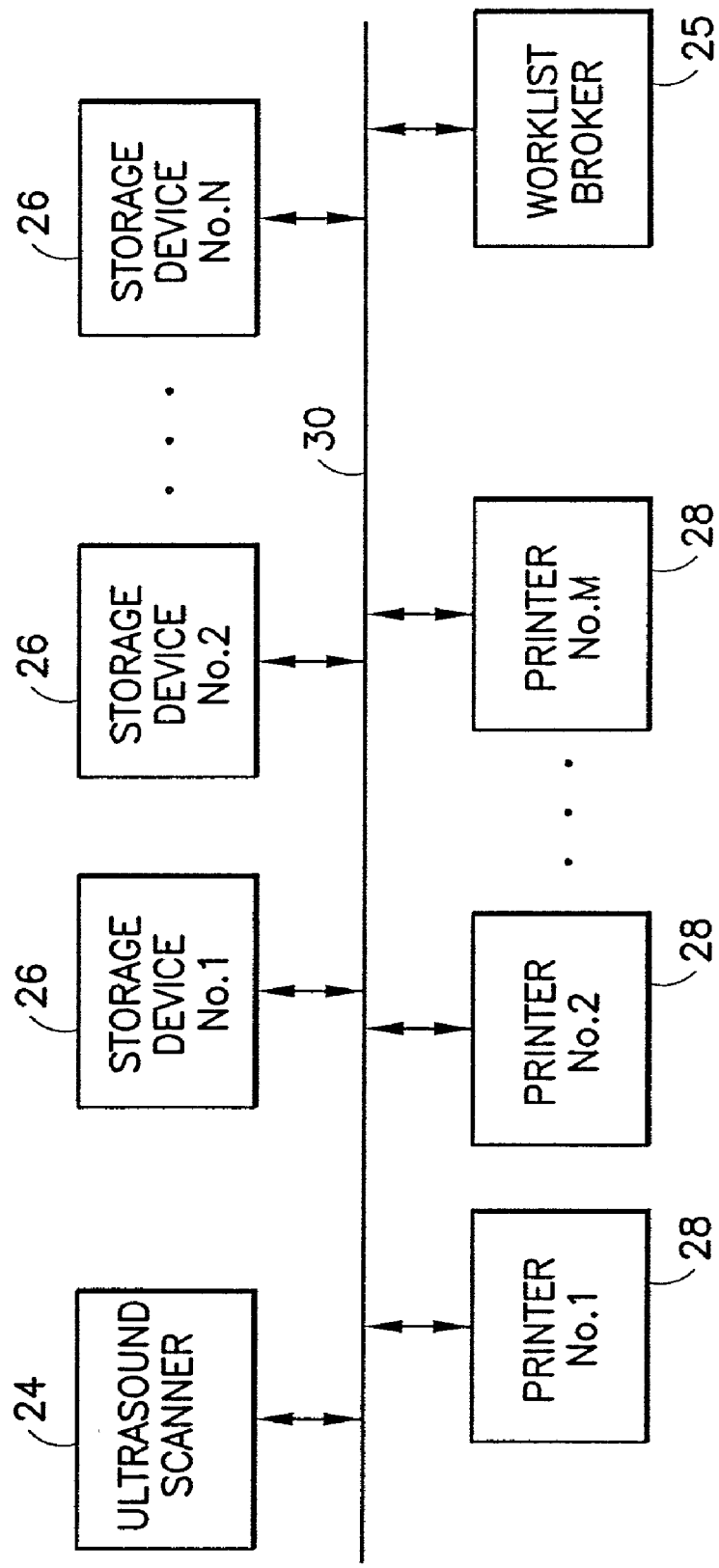
FIG. 2 is a block diagram generally depicting a typical DICOM network.

FIG. 2 generally depicts a simplified DICOM network having an ultrasound scanner 24, a worklist broker (e.g., an RIS) 25, N storage devices 26, and M printing devices 28, all connected to a local area network (LAN) 30. It will be readily appreciated that this diagram represents a simplified example of a DICOM network and that an actual DICOM network in the real world will have many more devices connected to the LAN, including modalities other than ultrasound imaging systems. The preferred embodiment of the invention is disclosed in the context of an imager (scanner) having the built-in capability to communicate with any one or more of the devices 25, 26 and 28 in conformance with the DICOM requirements. As used herein, the term "storage device" includes, but is not limited to, a picture archiving and communications system (PACS) having a viewing station.

Figure 3:
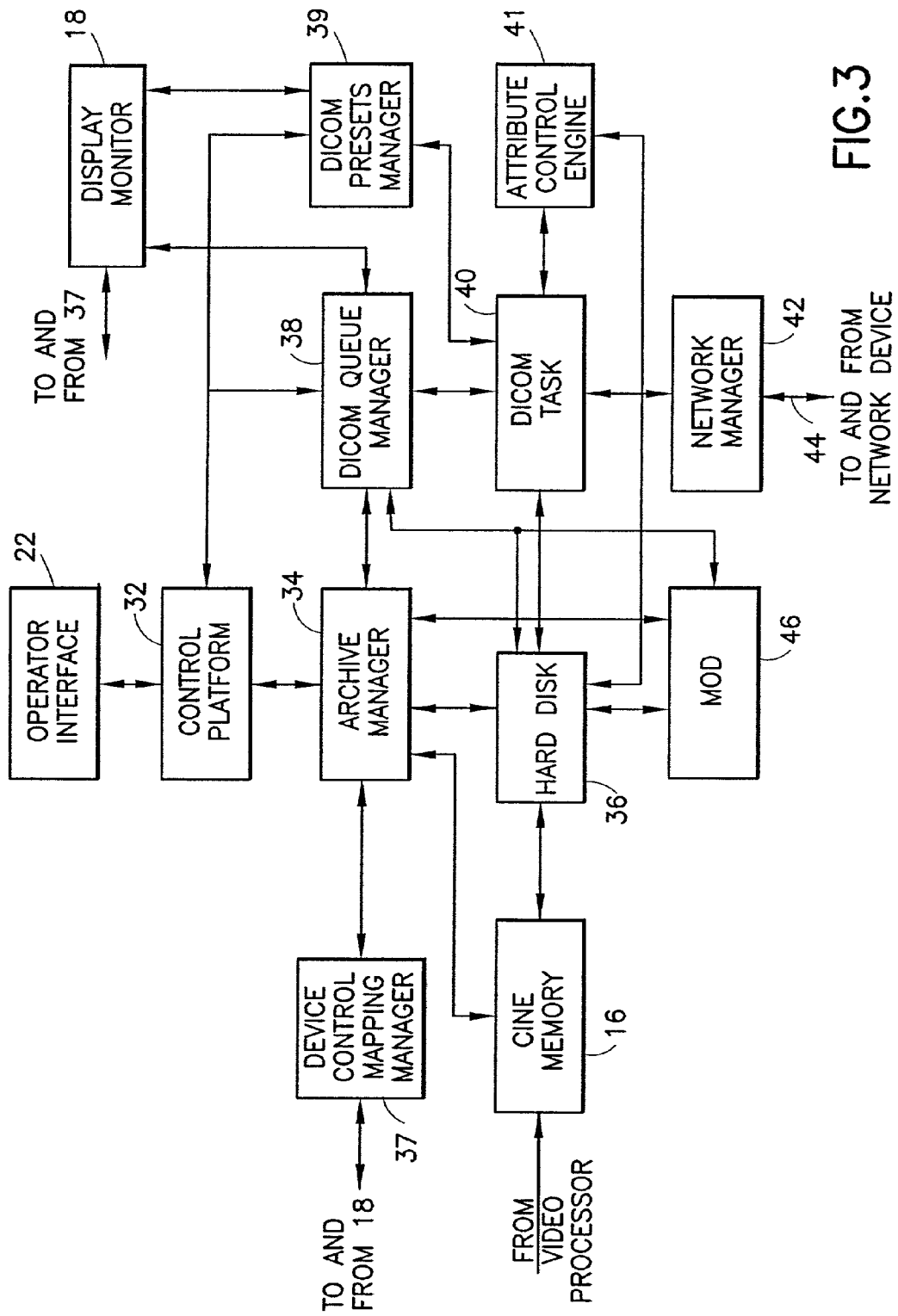
FIG. 3 is a block diagram generally depicting portions of the hardware and software of an ultrasound imaging system having DICOM capability.

A portion of an ultrasound imager having DICOM capability is generally depicted in FIG. 3. At the outset it should be appreciated that all of the blocks depicted in FIG. 3, with the exceptions of the cine memory 16, the display monitor 18, the operator interface 22 and the hard disk 36, are preferably, but not necessarily, incorporated in the host computer (depicted in FIG. 1 as block 20). It should be further appreciated that blocks 32, 34, and 37–42 in FIG. 3 are preferably, but not necessarily, implemented as software.

In the system depicted in FIG. 3, commands inputted via the operator interface 22 are detected and processed by a control platform 32. The imager partly shown in FIG. 3 is designed to communicate with a configured remote device only if that device has been "activated". Activation causes the DICOM presets manager 39 to configure one of a multiplicity of DICOM tasks 40 in accordance with configuration data entered into the system for the associated remote device. That particular DICOM task will thereafter remain configured for that type of remote device until reconfigured for a different device. Other DICOM tasks are configured for other remote devices.

Referring again to FIG. 3, the imaging system is equipped with a plurality of Print/Store buttons on the operator interface 22. Each Print/Store button can be configured by the device control mapping manager 37 to initiate image transfer to more than one remote device, e.g., when a particular Print/Store button is pressed, the computer will send the corresponding acquired image to all activated remote devices configured for that button. For each remote device configured to a particular Print/Store button, pressing that button after freezing an image will cause the associated DICOM task 40 to retrieve an image file having a copy of that image from the hard disk 36 and convert that image file to a DICOM object compatible with the associated remote device.

The device control mapping manager 37 constructs a mapping of DICOM tasks (configured for respective remote devices) to Print/Store buttons. The device control mapping manager 37 provides the device control mapping to the archive manager 34. When the archive manager later receives a posting from the control platform 32 that a particular Print/Store button has been pressed, the archive manager 34 will then refer to the device control mapping and determine the DICOM tasks associated with that button from the mapping. The archive manager 34 then advises the DICOM queue manager 38 which DICOM task 40 needs to construct objects incorporating the selected image frame. The DICOM queue manager 38 then copies that image file once for each task and, if the remote devices are storage devices or single-image printers, adds a job element to the Active Queue of each task.

Although FIG. 3 depicts only one DICOM task, in accordance with the preferred embodiment, the imager is typically programmed with multiple DICOM tasks. Typically one DICOM task is dedicated to worklist management and ten DICOM tasks are configured to convert image files into either DICOM print objects or DICOM storage objects. In response to pressing of a Print/Store button which is configured for multiple remote devices, a corresponding multiplicity of DICOM tasks will be started substantially simultaneously. These concurrently running tasks are performed using conventional multi-tasking principles.

Referring again to FIG. 3, each DICOM task 40 sends its DICOM object in proper format to the corresponding destination remote device via the network manager 42 and the port 44. Jobs which are waiting to be converted into DICOM objects by a DICOM task are queued. The queue is managed by a DICOM queue manager 38. When the DICOM task 40 receives a job from the queue, it will read a pointer which contains the file name of the image to be formatted and transferred to the destination remote device. The DICOM task 40 then retrieves the image from the named file on the hard disk and reformats it into the appropriate DICOM object in accordance with the instructions from the Attribute Control Engine 41. In addition to the pixel data for the image being transferred, the DICOM object constructed by the DICOM task will include attribute data in DICOM format, i.e., the image header. These attributes preferably include the following: Patient Name, Patient ID, Accession Number, Study Date, Study Time and Patient's Date of Birth. If the remote device is a storage device, the DICOM task will also include a Study Instance UID in the image header. The Study Instance UID typically is a concatenation comprising a vendor prefix, a product-specific number, a system serial number, and a study date and time.

Next the DICOM task 40 will open a connection (association) to the destination remote device and negotiate a syntax. In particular, the DICOM task 40 sends a request via the network manager 42 and a port 44 that an association with the configured remote device be opened. If the remote device responds affirmatively and if a communications syntax is agreed upon, the association is opened. Once the association is open and assuming that a channel on the network is available (i.e., the network is not busy), the image is sent from the imager onto the network, again via network manager 42 and port 44. If the destination remote device sends back a message that the image transfer was successful, then the DICOM task 40 notifies the queue manager 38. The queue manager then removes the entry for the successfully transferred image from the queue and deletes that image file from the hard disk 36.

As previously stated, each DICOM image is transferred to a storage device with an image header that includes the Study Instance UID, Patient Name, Patient ID, Accession Number, Study Date, Study Time and Patient's Date of Birth. The Patient Name, Patient ID, Accession Number and Patient's Date of Birth are entered manually on a New Patient screen by the system user. The New Patient screen is shown in FIG. 4. Each time the system user wants to start a new patient exam, the user presses a New Patient button on the keyboard. The user types a letter Y to verify that this is a new patient and then presses Return. A trackball is then used to select the appropriate exam category. The user then presses a Set button on the keyboard. The exam category selected determines the presets, available applications and worksheets. The user then fills in the appropriate patient data or, for DICOM users, presses ROI Size to go to a Worklist Schedule page (not shown). The trackball is used to select a patient from the worklist, then the user presses Set. The New Patient menu appears with the data filled in, including the data for the fields Patient Name, Patient ID, Accession Number, Patient's Date of Birth. The user then presses Exit. When Exit is pressed, the host computer automatically records the Study Date and Study Time, and automatically constructs the UID by concatenating the component information as previously described.

The graphical user interface further comprises worksheets and summary reports designed for specific areas of medical practice. For example, for obstetrics a Biometry Worksheet (not shown) displays measurements assigned to a calculation, while an Anatomy Worksheet (not shown) allows the system user to indicate which anatomy was imaged and its appearance. The Biometry Worksheet displays up to the last three values for each measurement used in the calculations and the results of new calculations computed from those measurements. An OB-1 Summary Report (shown in FIG. 5) displays information pertinent to a first trimester exam, while an OB-2 Summary Report (not shown) displays information pertinent to a second or third trimester exam. In the example presented in FIG. 5, the GA(LMP) field is gestational age, while the EDD(LMP) field is Clinical Estimated Date of Delivery, both of which are based on information entered in the OB New Patient menu (not shown). The Ultrasound Age is calculated from measured parameters. The Ultrasound EDD field is Ultrasound Estimated Date of Delivery calculated from measured parameters. To enter anatomical survey information, the system user types a "Y" to indicate each part of the anatomy which was imaged and an "N" to indicate that this part of the anatomy was not imaged. If a "Y" is typed in the Imaged? Field, the user must indicate whether the anatomy was normal ("N") or abnormal ("A"). Each Summary Report further includes a Comments field for entering up to three lines of comments.

The worksheets are viewed by clicking on a Reports softkey. The measurement data is used to calculate parameters which are displayed on the Summary Reports screens. The report data appearing on a Summary Report screen is automatically sent by the host computer to a serial port in ASCII format in response to the system user pressing a Print button on the keyboard while that same screen is being displayed. In accordance with the preferred embodiment of the invention, the DICOM Study Instance UID is attached to that report data sent to the serial port. As a result, the report data generated during a particular study can be accurately linked at the remote view station to transferred DICOM images from the same study.

The preferred embodiment of the invention will be described with reference to FIG. 6, which has a dashed rectangle representing of a storage device 26 of the type comprising a view station. The blocks outside of the dashed rectangle are components of an ultrasound imaging system. Blocks 14, 16, 18, 20 and 22 of the ultrasound imaging system have already been described with reference to FIG. 1. The hard disk 36 has already been described with reference to FIG. 3. The ultrasound imaging system in accordance with one preferred embodiment further comprises an Ethernet port 50 and an RS232 port 60.

Figure 6:
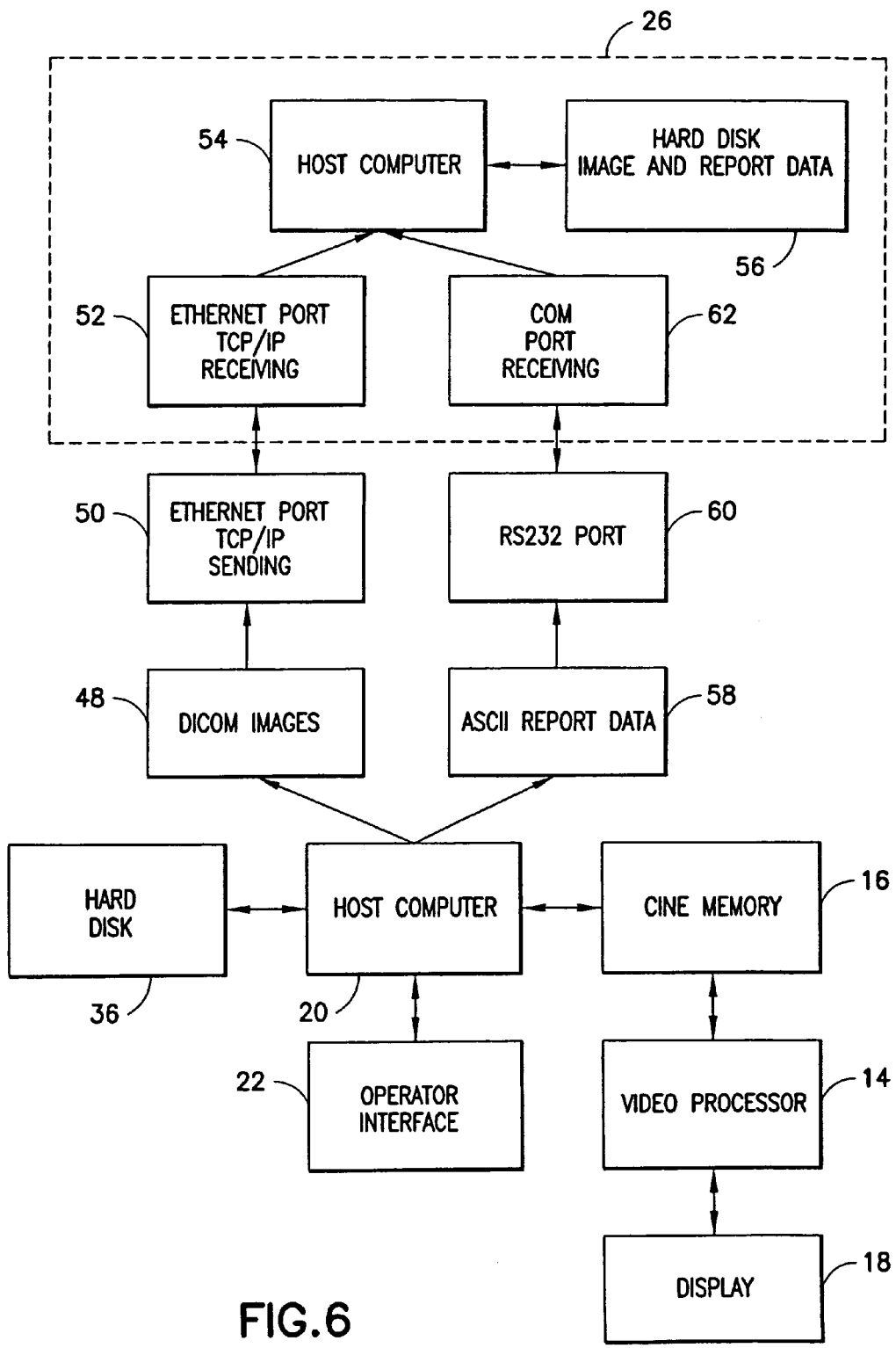
FIG. 6 is a block diagram showing the preferred embodiment of the present invention.

The storage device 26, shown in FIG. 6, comprises a host computer 54 and a hard disk 56 for storing image and report data. The host computer and hard disk may form parts of a personal computer. This personal computer further comprises an Ethernet port 52 for receiving image data and a COM port 62 for receiving report data. The Ethernet port 52 of the storage device is connected to the Ethernet port 50 of the ultrasound imaging system via a network, while the COM port 62 of the storage device is connected to the RS232 port 60 of the ultrasound imaging system via a network.

In accordance with the preferred embodiment of the invention, DICOM images 48 comprising an image header with a Study Instance UID are constructed by the host computer 20, transmitted from the Ethernet port 50, received by the Ethernet port 52, and stored on the hard disk 56 by the host computer 54. Also the host computer 20 attaches the same Study Instance UID to report data 58 in ASCII format. The report data with Study Instance UID are transmitted from the RS232 port 60 to the COM port 62. The report data is stored on the hard disk 56 by the host computer 54. The inclusion of the Study Instance UID in both the stored images and the stored report data allows the receiving view station to link the received report data acquired during a particular study with the received images acquired during the same study.

In accordance with the preferred embodiment, the host computer 20 is programmed to automatically construct and store the Study Instance UID when the system user exits the New Patient screen shown in FIG. 4. The host computer 20 is further programmed to automatically retrieve the stored Study Instance UID, attach it to the report data displayed on a Summary Report screen and then send the report data with attachment to the serial port in response to the system user pressing a Print button on the keyboard while that Summary Report screen is displayed.

In accordance with a further preferred embodiment, the host computer 54 of the receiving storage device 26 is programmed to link received report data which does not have the Study Instance UID attached to received images which do contain the Study Instance UID. This is accomplished as follows. After report data has been received, the host computer 54 detects whether a Study Instance UID is attached to the report. If not, then the host computer is programmed to search the hard disk 56 for any DICOM images that have attribute data which matches or nearly matches the attribute data in the unclassified report data. In accordance with the preferred embodiment, the following items are compared: Patient Name, Patient ID, Accession Number, Study Date, Study Time and Patient's Date of Birth. For each image having attribute data which almost matches all of the attribute data associated with the received report data, a dialogue box will appear on the screen of the view station, prompting the user to manually match an image with the report. Once the user has done so, the Study Instance UID in the matched image is copied and attached to the received report data and the report data with attachment is stored in memory, thereby creating a permanent link between that report and all images belonging to the identified study. This solution will provide an accurate link between studies (DICOM images and information) and report information without the need to update the existing software of any scanner which lacks the ability to transmit the Study Instance UID in ASCII format as part of report data transmitted via the serial port. For any scanner that is programmed to automatically attach the Study Instance UID to any ASCII report data, the view station can match images to reports by simply matching the Study Instance UIDs.

Although the disclosed preferred embodiment is an ultrasound scanner which communicates with remote devices using the DICOM protocol, it should be appreciated that the invention has application in scanners of other modalities and in scanners which use communication protocols other than DICOM. Currently, a number of modalities exist for medical diagnostic and imaging systems. These include computed tomography (CT) systems, x-ray systems (including both conventional and digital or digitized imaging systems), magnetic resonance (MR) systems, positron emission tomography (PET) systems, ultrasound systems, nuclear medicine systems, etc. In many instances, these modalities complement one another and offer the physician a range of techniques for imaging particular types of tissue, organs, physiological systems, etc. Health care institutions often arrange several such imaging systems at a single or multiple facilities, permitting its physicians to draw upon such resources as required by particular patient needs. Modern medical diagnostic systems typically include circuitry for acquiring image data and for transforming the data into a useable form, which is then processed to create a reconstructed image of features of interest within the patient. The image data acquisition and processing circuitry is sometimes referred to as a "scanner" if physical or electronic scanning occurs as part of the imaging process. The particular components of the system and related circuitry, of course, differ greatly between modalities due to their different physics and data processing requirements. The term "scanner" is used in the claims in the foregoing broad sense and is not intended to be limited to ultrasound scanners.

While the invention has been described with reference to preferred embodiments, it will be understood by those skilled in the art that various changes may be made and equivalents may be substituted for elements thereof without departing from the scope of the invention. In addition, many modifications may be made to adapt a particular situation to the teachings of the invention without departing from the essential scope thereof. Therefore it is intended that the invention not be limited to the particular embodiment disclosed as the best mode contemplated for carrying out this invention, but that the invention will include all embodiments falling within the scope of the appended claims.

The invention claimed is:

1. A scanner comprising:
   memory that electronically stores a study identifier that identifies a study, a frame of image data belonging to said study and report data belonging to said study;
   a parallel port;
   a serial port;
   means for associating said study identifier with said frame of image data in a first format;
   means for sending said frame of image data with said associated study identifier in said first format out said parallel port;
   means for associating said study identifier and said report data in a second format different than said first format; and
   means for sending said report data and said study identifier in said second format out said serial port.

2. The scanner as recited in claim 1, wherein said first format conforms to DICOM standards.

3. The scanner as recited in claim 2, wherein study identifier comprises a DICOM study instance unique identifier.

4. The scanner as recited in claim 1, wherein said second format is ASCII format.

5. The scanner as recited in claim 1, wherein said parallel port comprises an Ethernet connection.

6. The scanner as recited in claim 1, wherein said serial port comprises an RS232 interface.

7. The scanner as recited in claim 1, further comprising an image acquisition subsystem for acquiring said frame of image data, wherein said image acquisition subsystem comprises an array of ultrasound transducer elements.

8. The scanner as recited in claim 1, further comprising:
   a display monitor;
   means for displaying said frame of image data on said display monitor;
   means for measuring a feature in said displayed frame to acquire measurement data; and
   a user interface screen for displaying said measurement data on said display monitor,
   wherein said report data in said memory comprises said measurement data.

9. The scanner as recited in claim 1, further comprising:
   a display monitor;
   a patient information user interface screen displayed on said display monitor and comprising fields for entering patient information and an activatable exit field for requesting exit from said patient information user interface screen; and
   means for constructing said study identifier based at least in part on patient information entered on said user interface screen in response to activation of said exit field and then storing said study identifier in said memory.

10. A scanner comprising:
    memory that electronically stores a study identifier that identifies a study, a frame of image data belonging to said study and report data belonging to said study;
    a parallel port;
    a serial port; and
    a computer programmed to perform the following steps:
    associating said study identifier with said frame of image data in a first format;
    sending said frame of image data with said associated study identifier in said first format out said parallel port;
    associating said study identifier and said report data in a second format different than said first format; and
    sending said report data and said study identifier in said second format out said serial port.

11. The scanner as recited in claim 10, wherein said first format conforms to DICOM standards and said second format is ASCII format.

12. The scanner as recited in claim 10, wherein said parallel port comprises an Ethernet connection and said serial port comprises an RS232 interface.

13. The scanner as recited in claim 10, further comprising an array of ultrasound transducer elements.

14. The scanner as recited in claim 10, further comprising a user interface for entering report data and initiating transfer of said report data to said serial port, wherein said computer is further programmed to join said study identifier with said report data in response to initiation of transfer of said report data to said serial port.

15. A method for transmitting linked images and reports from a computerized system, comprising the steps of:
    electronically storing a study identifier that identifies a study, a frame of image data belonging to said study and report data belonging to said study;
    associating said study identifier with said frame of image data in a first format;

sending said frame of image data and said study identifier in said first format out a parallel port of said computerized system in response to a first system user command input;

associating said study identifier with report data in a second format different than said first format; and sending said report data and said study identifier in said second format out a serial port of said computerized system in response to a second system user command input.

16. The method as recited in claim 15, wherein said first format conforms to DICOM standards.

17. The method as recited in claim 16, wherein study identifier comprises a DICOM study instance unique identifier.

18. The method as recited in claim 15, wherein said second format comprises ASCII format.

19. The method as recited in claim 15, wherein said parallel port comprises an Ethernet connection.

20. The method as recited in claim 15, wherein serial port comprises an RS232 interface.

21. A view station comprising:
a display monitor;
a user interface;
a data port;
memory; and
a computer programmed to perform the following steps:
storing frames of image data in said memory, each frame having associated therewith a respective study identifier identifying the particular study to which said frame belongs;
receiving report data via said data port;
detecting report data having no study identifier associated therewith;
searching said frames of image data for a frame having attributes associated with said image data which closely match attributes associated with said report data;
generating a message on said display monitor requesting confirmation that said report data should be linked to said frame having said closely matching attributes; and
associating said study identifier with said report data in response to receipt of a user input indicating confirmation via said operator interface.

22. A method for linking images and report data in a computerized system, comprising the steps of:
storing frames of image data, each frame having associated therewith a respective study identifier identifying the particular study to which said frame belongs;
receiving report data;
detecting whether said received report data has no study identifier associated therewith;
searching said frames of image data for a frame having attributes associated with said image data which closely match attributes associated with said report data;
displaying a message requesting confirmation that said report data should be linked to said frame having said closely matching attributes; and associating said study identifier with said report data in response to receipt of confirmation.

23. A scanner comprising:
an image acquisition system;
a display monitor;
an operator interface comprising movable input elements that are physical components and graphical user interface elements that are activatable only when displayed on said display monitor;
memory for storing data; and
a computer programmed to perform the following steps:
displaying a first graphical user interface screen on said display monitor in response to a first command inputted via said operator interface, said first graphical user interface screen comprising fillable fields for patient information and selectable-fields representing examination categories;
exiting said first graphical user interface screen, recording the current date and time, and constructing a study identifier comprising said date, said time and a scanner identifier that identifies said scanner in response to a second command inputted via said operator interface;
storing said study identifier in said memory;
storing a frame of image data acquired by said image acquisition system in said memory in response to a third command inputted via said operator interface;
retrieving said frame of image data and said study identifier from said memory and constructing a data object comprising said frame of image data and said study identifier in a first format in response to a fourth command inputted via said operator interface;
displaying a second graphical user interface screen on said display monitor in response to a fifth command inputted via said operator interface, said second graphical user interface screen comprising fields filled with report data acquired during a study identified by said study identifier; and
retrieving said study identifier from said memory and constructing a file comprising said study identifier and said report data in said filled fields in a second format different than said first format in response to a sixth command inputted via said operator interface.

24. The scanner as recited in claim 23, wherein said computer is further programmed to perform the following steps:
sending said data object to a first output port, addressed to a pre-designated remote device, in response to said fourth command; and
sending said file to a second output port, addressed to said pre-designated remote device, in response to said sixth command.

* * * * *